United States Patent [19]

Gwatkin

[11] 3,992,520

[45] Nov. 16, 1976

[54] ANTI-FERTILITY VACCINE COMPRISING SOLUBILIZED ZONA PELLUCIDA AND ANTI-SERUM

[75] Inventor: Ralph B. L. Gwatkin, Maplewood, N.J.

[73] Assignee: Merck & Co., Inc., Rahway, N.J.

[22] Filed: Nov. 27, 1974

[21] Appl. No.: 527,725

[52] U.S. Cl. .................................. 424/85; 424/88; 424/105
[51] Int. Cl.$^2$ ........................................ A61K 39/00
[58] Field of Search ...................... 424/105, 88, 85

[56] References Cited
UNITED STATES PATENTS

| | | | |
|---|---|---|---|
| 1,978,298 | 10/1934 | Eldred | 424/105 |
| 2,983,648 | 5/1961 | Neumann | 424/105 |

OTHER PUBLICATIONS

Theurer — Chem. Abst., vol. 76, (1972), p. 138961q.
Swanson et al. — Chem. Abst., vol. 76, (1972), p. 10725y.

*Primary Examiner*—Sam Rosen
*Attorney, Agent, or Firm*—Harry E. Westlake; James A. Arno; Frank M. Mahon

[57] ABSTRACT

A vaccine for immunological control of fertility is disclosed comprising solubilized mammalian zona pellucida; also disclosed are antisera specific against the antigenic mammalian zona pellucida; processes for the preparation of such vaccine and antisera; and methods of treatment comprising administering such vaccine and antisera for the immunological control of fertility.

7 Claims, No Drawings

ANTI-FERTILITY VACCINE COMPRISING SOLUBILIZED ZONA PELLUCIDA AND ANTI-SERUM

BACKGROUND OF THE INVENTION

This invention relates to immunological control of fertility utilizing the antigenic, noncellular proteinaceous coating of the mammalian egg, the zona pellucida. The invention also relates to a water-soluble form of the zona pellucida; hereinafter referred to as "solubilized zona pellucida" or "SZP" for convenience. The invention further relates to vaccines comprising solubilized mammalian zona pellucida; to antisera comprising antibodies against the antigenic protein which constitutes the zona pellucida; to processes for the preparation of such SZP, vaccines and antisera; and to methods of treatment comprising administering such vaccines and antisera for fertility control in the mammalian female.

The possibility of utilizing immunological procedures for fertility control both in the male and in the female has been much discussed, but to date none has proved feasible. Such prior art attempts are characterized by an inability to isolate an antigenic material in pure form, which is a necessary condition for the production of tissue specific antibodies. Another shortcoming of such prior art attempts is that antisera substantially specific to a certain genital tissue are species specific, that is, such antisera give no evidence of immune reaction with the analogous tissue from distinct animal species; such results additionally characterize the species-specificity of prior art antigen preparations. The requirements imposed upon any immunological approach to fertility must include tissue specificity and cross-reaction (as opposed to species-specificity) because unless there is tissue specificity the immunological procedure could not be considered safe and without cross-reaction any such immunological procedure would be extremely limited since the antigenic source material would have to be obtained from the species to be rendered infertile —an impossibility for fertility control of the human female.

The possibility of immunological control of fertility employing the antigenic mammalian zona pellucida has been considered. This structure, the zona pellucida, and the phenomena associated with it, including the "zona reaction", have been much studied in reproductive biology with respect to certain sperm-egg interactions: *approach*, *attachment* and *penetration*. *Approach* of sperm to egg appears to be a random process without numerical limit. *Attachment* (sperm to zona pellucida) appears to be attributable to definite sperm receptor sites on the surface of the zona and in all likelihood is limited numerically by available area. *Penetration*, however, is normally limited to a single sperm. On penetration the receptor sites are deactivated (zona reaction). If the receptor sites or sites peripheral thereto are antigenic, the possibility of creating antibodies which mask or alter the zona pellucida and thus preclude attachment and penetration is an attractive, non-hormonal approach to fertility control. But to date such an approach has fallen to the above discussed two hurdles, namely: species-specificity and lack of tissue specificity. While Applicant is bound by no theory, it would appear that such prior attempts were unsuccessful principally because the precise antigenic material critical for practice of the present invention was not obtained in functional form by prior art procedures which typically comprise gross saline extraction of macerated whole ovarian tissue. Antisera prepared from such saline extracts, although rendered to some degree ovary-specific by adsorption of unwanted antibodies by contacting with diverse somatic tissues, invariably are found species-specific; further it is extremely doubtful that such prior art antisera are even capable of entering into an immune response with the critical antigenic sites of the zona pellucida for reasons which will be made evident below.

Unexpectedly it has been discovered that a tissue specific, non-species dependent (cross-reacting) anti-fertility vaccine can be prepared from the mammalian zona pellucida by a process which comprises heating either zonae pellucidae, per se, intact eggs or ovarian tissue comprising eggs in an appropriate medium such as water such that the proteinaceous zona pellucida is solubilized. Such aqueous solutions comprising solubilized zona pellucida may be evaporated to dryness to provide a form of the zona protein which is readily again solubilized in aqueous solution. Thus for purposes of the present invention the term "solubilized zona pellucida" (SZP) is defined to embrace mammalian zona pellucida protein — dry or in solution — which has been rendered water soluble according to the method of the present invention. Antibodies prepared from such solubilized zona pellucida are not species-specific and specifically react with the zona pellucida of the mammalian animal being treated for fertility control.

Thus, it is an object of the present invention to provide a vaccine for immunological fertility control of the female mammal which provides a reversible state of infertility without disruption of the normal estrus cycle. A further object of the present invention is to provide such a vaccine for immunological fertility control of the female mammal comprising solubilized mammalian zona pellucida (SZP) and to provide antisera comprising antibodies ("anti-SZP") against the antigenic mammalian zona pellucida for fertility control; wherein said vaccine and antisera are tissue specific and are active across mammalian species lines. Further objects of the present invention are to provide processes for the preparation of such vaccine, antisera (including SZP and anti-SZP, per se) and to provide methods of treatment comprising administering such vaccine and antisera for immunological control of fertility in the mammalian female.

DETAILED DESCRIPTION OF THE INVENTION

The various aspects of the present invention — vaccine and antisera pharmaceutical compositions (including SZP and anti-SZP, per se), methods for the preparation of such pharmaceutical compositions, and methods of administering such compositions for the immunological control of fertility — will first be stated and described. There following will be a presentation of technical data and techniques which specifically describe the present invention in all of its aspects including physical and chemical characterization of the solubilized, isolated antigenic mammalian zona pellucida; vaccines and antisera prepared therefrom; and the effects of such preparations on fertility of the mammalian female. Such specific characterizing data and techniques representatively state the general principles involved in practicing the first-described aspects of the present invention and from such representative teachings one will be enabled to practice the present invention in all of its express and implied embodiments.

VACCINE

The vaccine of the present invention provides immunological control of fertility when administered to the female mammal by methods hereinafter described. Compositionally the vaccine comprises solubilized mammalian zona pellucida derived from a nonself source. The nonself source requirement exists because eggs, unlike sperm, are present early in fetal development and thus the female is tolerant to its own zonae pellucidae, the noncellular proteinaceous coating which surrounds the mammalian ovum. As described below, there is no criticality as to the source of the zona pellucida for practice of the present invention with the sole proviso given above that the solubilized zona pellucida be obtained from an animal species distinct from the one to be treated for fertility control. Thus for example, for immunization of the human female, practical source animals for zonae pellucidae include practically any lower mammalian species such as the laboratory hamster, or laboratory mouse but for practical reasons slaughter house sources such as cow, sheep and pig may be preferred depending on availability. The vaccine comprises an aqueous solution of the solubilized mammalian zona pellucida (SZP), either alone or combined with suitable adjuvant such as aluminum hydroxide, mineral oil-water emulsion or emulsifiers such as calcium alginate. The particular adjuvant is not critical. The vaccine composition may be prepared in unit dosage form or in bulk form for ultimate dilution. Alternately, the vaccine may be prepared in dry form (lyophilized) from the solubilized form for convenience of storage.

The dosage form of the vaccine may be prepared from the bulk solution by dilution with sterile water or with buffered aqueous adjuvant (preferred pH 7.0 to 7.2) such that the unit dosage by injection comprises SZP in the range of from about 1.0 to about 10.0 µg. per kg. of body weight. Method of treatment aspects for effective vaccination, i.e., period and number of unit injections, will be described below.

ANTISERA

The antisera compositions of the present invention comprise antibodies against the antigenic zona pellucida and such compositions are useful as a passive means of immunological control of fertility since inoculation with such antibody provides short term infertility and additionally appears to prevent uterine implantation of fertilized ova. The methods of preparing such antisera and methods of administering it are described below. Compositionally the antisera comprise the identified antibody in cell-free sera or fractions thereof (Cohn fractions or lyophilized form).

Well-known analytical techniques for characterizing the quality and quantity of such vaccine and antibody preparations, anti-SZP, include for example:
1. Gel Immunodiffusion [Ouchterlony, 26 *Acta, Pathol, Microbiol, Scand*, 507 (1949)];
2. Sandwich Technique, employing Fluorescent Antibody [Coombs, *Immunological Methods*; ed. by Ackroyd; Blackwell; Oxford (1964)]; and
3. Inhibition of In Vitro Fertilization [Gwatkin, et al., 30 *J. Reprod. Fert.* 389 (1972)].

METHOD OF TREATMENT

In the method of treatment aspect of the present invention it is to be emphasized that the precise dosage level and period of inoculation depend upon the case history of the individual being treated and in the last analysis are left to the routine determination of the skilled therapist because such parameters are readily determined by the general guidelines given here. In general, vaccination with the instant vaccine comprising solubilized mammalian zona pellucida provides for a reversible state of infertility of the female being treated typically lasting from about 15 to about 30 weeks. Typically, immunization (infertility) in the human female is achieved by injection with vaccine solution comprising from about 70 to about 700 µg. of SZP given once or repeated after an interval of from 7 to 14 days. The state of immunity and therefore of infertility may be determined by obtaining a small blood sample and titrating the serum portion thereof by gel immunodiffusion against SZP. Agglutination at a titer of greater than 1:16 indicates a sufficiently high antibody level to insure infertility. The return of fertility is indicated by a sharp drop in antibody titer.

The method of treatment comprising administering the above-described antisera is, in the case of treatment of the human female, by injection of a globulin-rich fraction of serum from an immunized animal such as the horse, sheep, pig and the like. Such fraction is prepared by cold-alcohol precipitation (Cohn method) and typically the unit dose by injection comprises from about 10 to about 20 mg./kg. body weight. One injection given up to about 14 days after coitus with the possibility of conception is typically sufficient to prevent pregnancy, although repeated injections given daily up to the fourteenth day give added assurance of effectiveness. Alternately the anti-SZP compositions may be used as a means of short-term control of fertility. Unit dosage by injection of from about 10 to about 20 mg./kg. body weight of the above-described fraction provides an infertile state lasting at least 5 days, the return of fertility being determined as described above.

VACCINE, METHOD OF PREPARATION

As previously indicated there is no criticality as to the source of the mammalian zona pellucida, but for practical reasons the following species of animals are preferred for the harvest of zonae pellucidae for the preparation of vaccine to be used in humans and in domesticated animals: laboratory animals such as mice, hamsters, rats and rabbits and slaughter house animals such as cow calves, sheep and pigs.

Solubilization of the zona pellucida is achieved by heating intact zonae at from about 65° to about 100° C. in an aqueous medium alternately comprising phosphate buffered saline (PBS, having the composition in g/l: $CaCl_2$ 0.1; KCl 0.2; $KH_2PO_4$ 0.2; $MgCl_2·6H_2O$ 0.1; $N_2Cl$ 8.0; $Na_2HPO_4·2H_2O$ 1.15) or similarly buffered saline solutions providing a pH of from about 7.0 to about 7.4. As a practical matter the solubilization of the proteinaceous zona pellucida may be performed directly upon gross ovarian tissue which has been mechanically comminuted prior to heating. Preferably, the ovarian tissue is obtained from immature animals since the number of zonae-bearing oocytes decreases rapidly with age. Alternately, and in the instance of of small scale preparations, the zonae may be mechanically separated from the ova. This may be accomplished, for example, by drawing the complete ova through an aperture approximately ½ to ¾ its normal diameter. By such a process the zona is ripped from the ova as it is pulled through the aperture.

The zona pellucida thus solubilized may be further isolated or purified from contaminating matter by the following generalized procedure: centrifugation; dialysis of the resulting clear solution through cellophane in an aqueous bath; followed by column chromatography. Active SZP fractions off such a column are identified by standard procedures previously enumerated such as immunodiffusion and in vitro fetilization assay.

The purity of the resulting SZP may be determined by any of the following well-known procedures:
1. Ultracentrifugation;
2. Electrophoresis on Agarose-Acrylamide Composite Gels [7 *Biochemistry* 668 (1968)];
3. Inhibition of Hamster Fertilization In Vitro; and
4. Immunodiffusion against antiserum specific for the zona protein.

ANTISERA, METHOD OF PREPARATION

In general the antisera compositions of the present invention are prepared by injecting into a host animal the solubilized zona pellucida of a distinct donor species and thereafter collecting serum antibodies. More particularly the following procedure is employed: A suitable animal such as the horse, sheep or goat receives an intramuscular injection of SZP in solution (5–10 μg. SZP/Kg. body weight) in 0.5–1.0 ml. complete Freund's adjuvant). Starting 10 days later similar injections are given in incomplete Freund's adjuvant at 10 day intervals. The animals are bled at these times and the titer of antibody is measured by immunodiffusion against purified SZP.

The following examples specifically illustrate but do not limit the pharmaceutical composition, and method of treatment aspects of the present invention. In fact the following specific examples describe procedures which are generally applicable — requiring but noncritical modifications to practice all express and implied embodiments of the present invention.

EXAMPLE 1

PREPARATION AND PROPERTIES OF SOLUBILIZED HAMSTER ZONA PELLUCIDA AND ANALYTICAL TECHNIQUES

Hamster zonae are isolated from intact ova by a rupture technique. In this technique individual ova are drawn through a narrow aperture (60 μ bore pipet) such that the zona coat ruptures and separates from the intact ovum (vitellus). Two thousand zonae pellucidae thus obtained are placed in 100 micro liters of aqueous phosphate buffered saline [PBS; 99 *J. Exp. Med.* 167 (1954)] and heated at 65° C. for 35 minutes whereupon the zonae are completely dissolved to provide a clear solution. Ultracentrifugal analysis shows the solution to contain a single molecular species with a molecular weight of $8.9 \times 10^6$. The molecular species is a protein, consisting of 17 amino acids. (Table I).

TABLE I

AMINO ACID COMPOSITION OF HAMSTER ZONA PROTEIN

| Amino Acid | % Total Amino Acids |
|---|---|
| TYR | 9.31 |
| PHE | 10.40 |
| LYS | 6.78 |

TABLE I-continued

AMINO ACID COMPOSITION OF HAMSTER ZONA PROTEIN

| Amino Acid | % Total Amino Acids |
|---|---|
| HIS | 4.88 |
| ARG | 2.11 |
| ASP | 4.27 |
| GLU | 7.77 |
| THR | 6.99 |
| SER | 6.71 |
| PRO | 5.89 |
| ALA | 5.23 |
| GLY | 6.54 |
| VAL | 7.25 |
| CYS | 0.92 |
| MET | 0.32 |
| ILE | 0.24 |
| LEU | 14.38 |

Consistent with the amino acid composition, the hamster zona protein (hamster-SZP) is found to be neutral or weakly basic. Gel electrophoresis of the hamster-SZP protein thus obtained (10% polyacrylamide; pH 7.0; 2 milliamps per 5 mm diameter tube) fails to move the protein after 18 hours — the sample remaining as a single band at the top of the gel column. The band stains deeply with protein stain (fast green). The band does not stain with alcian blue, suggesting that the SZP protein contains little or no carbohydrate. On treating the hamster-SZP with urea and mercaptoethanol, it disassociates into three lower sub-units of molecular weights 100,000, 80,000 and 55,000 as revealed by migration in the above-described electrophoresis gel; the disassociation is effected by heating at 50° C. for 45 minutes a mixture of 10 μl of hamster-SZP, one drop glycerol and 10 μl of a solution, which comprises 100 mg. sodium dodecyl sulfate, 2.4 g. urea, 100 μl 1.2% aqueous mercaptoethanol, and 10 ml. distilled water; thereafter the mixture is applied to a 10% gel for electrophoresis against reference standards.

An analytical procedure for determining the activity of the hamster-SZP is by assessing its interaction with capacitated hamster spermatozoa. By capacitation is meant sperm which are capable of penetrating the zona pellucida for ultimate fertilization of the egg. Capacitation of sperm in vitro is routinely effected by treating sperm obtained from the epididymis for 6 hours in a tissue culture medium containing cumulus cells obtained from the oviduct of super ovulated animals 20 hours after the injection of 30 I.U. HCG [Gwatkin, et al., 30 *J. Reprod. Fert.* 389 (1972)]. When such capacitated spermatozoa are incubated with hamster-SZP, the extent to which the spermatozoa are incapable of penetrating cumulus-free eggs is a measure of the activity of the SZP. For example, the activity of the above-described hamster-SZP is determined by adding 10 μl of the solution comprising it to 30 μl of the solution comprising the capacitated hamster spermatozoa, $5 \times 10^6$ sperm per ml. After a 30 minute incubation, 20 cumulus-free hamster eggs are added and sperm penetration is scored after a 90 minute interval. Capacitated spermatozoa pretreated with hamster-SZP, although motile, are completely incapable of penetrating the eggs. When mouse-SZP obtained from the laboratory mouse by an identical procedure is substituted for the hamster-SZP, positive results are obtained in the above-described assay. This provides evidence that SZP is not species specific. A second, direct, indication of cross-reaction (lack of species specificity) is provided by immunization against fertility, described below, wherein it is shown that vaccination of distinct animal species, ranging from the laboratory mouse to various primates, with hamster-SZP renders such animal species infertile as observed on natural matings and as observed by immunofluorescence of eggs taken from laparotomized species which had been vaccinated (primates).

Another analytical assay comprising immunofluorescence of eggs treated with antisera against solubilized zona pellucida also indicates the lack of species specificity of the instant vaccine. Thus, for example, antiserum prepared in mice against the above-described hamster-SZP reacts with eggs of hamster, mouse, cow, rhesus monkey and squirrel monkey. Said reaction being evident when the eggs are treated with fluorescent anti-mouse globulin; however the concentration of the antiserum required to produce fluorescence varies with the species.

Vaccination of female hamsters with the above-described hamster-SZP produced, as expected, no detectable immune response, but when female mice are given vaccine injections (the vaccine comprising 4 μg hamster-SZP in 0.5 ml. Freund's Adjuvant — complete first injection, incomplete for subsequent injections) intramuscularly and again at 10-day intervals for a total of 4 injections serum analysis, as described above, shows that antibodies against the zona pellucida are established. When these mice are mated, the animals are found infertile.

To demonstrate the lack of species-specificity in the immune response, antisera collected from the vaccinated mice are collected according to the following procedure: A glass micro-pipet is inserted into the orbital sinus and blood is allowed to flow into the pipet. This blood is transferred to a glass tube and allowed to clot and then centrifuged at 1,000 g. for 5 minutes. The serum is decanted and stored at 5° C. When such sera comprising anti-SZP antibodies are assayed for interaction with species-diverse mammalian eggs (hamster, mouse, cow, squirrel monkey, and rhesus monkey), a bright fluorescent is observed on the zona pellucida of eggs so treated when exposed to fluorescent anti-mouse globulin. However, the antibody-antigen reaction is specific to the zona pellucida structure for when the same antiserum is contacted with diverse tissues such as hamster cornea, hamster eggs without zona, hamster cumulus cells and hamster sperm no immune reaction is seen. These results constitute yet another analytical means for assaying vaccine and antisera preparations and in determining the effectiveness of vaccination. A further analytical procedure for determination of purity of the solubilized mammalian zona pellucida is to conduct immunodiffusion and immunoelectrophoresis evaluations wherein the interaction of the SZP with an antibody produced therefrom is observed. With respect to the above-described hamster-SZP and the antiserum, it is observed that a single precipitin band is formed, thus indicating that the solubilized zona pellucida consists of a single antigen.

EXAMPLE 2

ISOLATION OF SZP FROM OVARIES AND VACCINE PREPARATION

Whole ovaries (100) from cow calves (ranging in age from 5–7 months) are collected on ice from the slaughter house. Each ovary comprises approximately 180,000 follicles from which approximately 2.0 mg. of zona protein is present. The ovaries are minced with scissors and for each gram wet weight thereof is added 5.5 ml. of Dulbecco's Phosphate Buffered Saline (PBS) [99 J. Exp. Med. 167 (1964)]. The mixture is homogenized for 1 minute in a Sorval Omnimixer cooled with ice. The homogenate is poured off into 25 ml. pyrex centrifuge tubes which tubes are placed in a boiling water bath for 15 minutes. The tubes are then centrifuged at 12,000 g. for 8 minutes. The resulting clear supernatant is poured off and the pellet is discarded. The supernatant in cellulose dialysis tubing is dialyzed against a 100 × volume aqueous medium of 0.01M ammonium bicarbonate overnight at 5° C. The dialyzed material is lyophilized. The lyophilized extract is dissolved in the minimum amount of PBS for placement on a chromatographic column loaded with Biorad's Biogel A–5M, to achieve a separation of SZP from lower molecular weight species having a molecular weight below $5 \times 10^6$. Active fractions, eluted with PBS, (fractions comprising cow-SZP) are identified by immunodiffusion and in vitro fertilization assay. The active fractions are then placed on a chromatographic column loaded with Biogel A50M, which separates over the molecular weight range $10^6$ to $5 \times 10^7$. The active fractions are again identified by immunodiffusion and in vitro fertilization assay. The active fractions, so identified, give a single band against anti-SZP serum (mouse) which intersects the band found with hamster-SZP, indicating immunological identity. The active fractions block hamster egg fertilization in vitro. The resulting fractions comprising cow-SZP in solution are lyophilized for later use.

A vaccine suitable for immunological control of fertility in the human female in unit dosage form by intramuscular injection is prepared by dissolving 500 μg of the above-prepared cow-SZP (lyophilized form) in 1.0 ml. of sterile PBS solution.

What is claimed is:

1. Water solubilized zona pellucida prepared by heating mammalian zona pellucida at a temperature of from about 65° C. to about 100° C. in an aqueous medium comprising buffered saline solution providing a pH of from about 7 to about 7.4 until a clear solution is obtained.

2. A vaccine for immunological control of fertility in the female mammal comprising an aqueous solution containing an anti-fertility effective quantity of water solubilized zona pellucida of claim 1.

3. A method for the immunological control of fertility in the female mammal which comprises administering by injection an aqueous solution containing an anti-fertility effective amount of water solubilized zona pellucida of claim 1.

4. An anti-serum composition for control of fertility in the female mammal comprising cell-free sera containing an anti-fertility effective amount of the antibody obtained by injecting into a mammalian host animal the water solubilized zona pellucida of claim 1 of a distinct donor species and thereafter collecting from said host the cell-free sera containing the serum antibodies.

5. An injectable pharmaceutical composition for control of fertility in the female mammal comprising cell-free sera containing an anti-fertility effective amount of the antibody of claim 4.

6. A method for the immunological control of fertility in the female mammal comprising administering by injection a pharmaceutical composition comprising cell-free sera containing an anti-fertility effective amount of the antibody of claim 4.

7. A process for preparing an anti-fertility vaccine for immunological control of fertility in the female mammal comprising solubilizing mammalian zona pellucida in an aqueous medium comprising buffered saline solution providing a pH of from about 7 to 7.4 by heating said zona pellucida in said medium at a temperature of from about 65° C. to about 100° C. until a clear solution is obtained.

* * * * *